(12) United States Patent
Murphy et al.

(10) Patent No.: US 8,051,727 B1
(45) Date of Patent: Nov. 8, 2011

(54) PORE-WATER PROFILER

(75) Inventors: Fred Murphy, San Jose, CA (US); James S. Kuwabara, Menlo Park, CA (US); Brent R. Topping, San Jose, CA (US); Francis Parchaso, San Francisco, CA (US); Robert C. Myhre, Hillborough, CA (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 838 days.

(21) Appl. No.: 12/107,331

(22) Filed: Apr. 22, 2008

(51) Int. Cl.
*G01N 1/10* (2006.01)
(52) U.S. Cl. ..................................... 73/864.74
(58) Field of Classification Search .................. None
See application file for complete search history.

(56) References Cited

U.S. PATENT DOCUMENTS

| | | | |
|---|---|---|---|
| 4,157,664 A * | 6/1979 | Robinson | 73/864.64 |
| 4,288,206 A | 9/1981 | Tigwell et al. | |
| 5,520,046 A * | 5/1996 | Sornein et al. | 73/152.23 |
| 5,587,538 A * | 12/1996 | Bratton | 73/863.33 |
| 5,889,217 A * | 3/1999 | Rossabi et al. | 73/864.74 |
| 6,840,121 B2 | 1/2005 | Thomas et al. | |
| 7,318,911 B2 * | 1/2008 | Smith | 422/100 |

OTHER PUBLICATIONS

F.L. Sayles et al., "In Situ Sampler for Marine Sedimentary Pore Waters: Evidence for Potassium Depletion and Calcium Enrichment," Science, New Series, vol. 181, No. 4095, Jul. 13, 1973, pp. 154-156.

Francis J. Sansone, Heather L. Spalding, and Celia M. Smith. Limnol. Oceanogr. Methods (2008) 6:119-125.
Kuwabara, J. et al., "Quantifying the Benthic Source of Nutrients to the Water column of Upper Klamath Lake, Oregon," USGS Open File Report 2007-1276, 2007, 39 pp.
KC Denmark Multi-water Sampler, 2 pp.
Kolling, M. et al., "Rhizon—An Excellent Pore Water Sampler for Low Maintenance Collection and Filtration of Small Volume Samples," EGU General Assembly, abstract, 1 p.
Kolling, M. et al., "Rhizon—An Excellent Pore Water Sampler for Low Maintenance Collection and Filtration of Small Volume Samples," EGU General Assembly, Apr. 2005.
Morford, J.L. et al., "Insights on Geochemical Cycling of U, Re and Mo from Seasonal Sampling in Boston Harbor, Massachusetts, U.S.A.," Geochim. Cosmochim. Acta (2006), doi: 10.1016/j.gca.2006.10. 016, submitted on Mar. 17, 2006, accepted on Oct. 23, 2006, 63 pp. (see p. 8).

(Continued)

*Primary Examiner* — Robert Raevis
(74) *Attorney, Agent, or Firm* — C. Joan Gilsdorf

(57) ABSTRACT

A pore-water profiler and method for sampling pore water. The pore-water profiler includes a sample intake probe that receives the fluid to be sampled. A clog-resistant first filter filters the fluid as it enters the sample intake probe. A second filter, which has a pore size less than the pore size of the first filter, filters the fluid a second time before the fluid enters a sample container. A sample triggering system connected to the sample container initiates sampling by causing the fluid to be drawn into the sample intake probe. The profiler provides high-resolution (centimeter-scale) vertical pore-water profiles. The sequential filtration of the pore water avoids the problem of sample-circuit clogging, even in sediments dominated by fine or organic-rich particles. The profiler has all non-metallic, acid-washable components that contact the fluid sample, making the profiler suitable for trace-inorganic studies.

13 Claims, 9 Drawing Sheets

OTHER PUBLICATIONS

SSC San Diego, "Coastal Contaminant Migration Monitoring: The Trident Probe and UltraSeep System," Technical Report 1902, Jun. 2003, 56 pp. (see pp. 4-6 and 16).

Manning Environment Corporation (Santa Cruz, California), Model S-4050 Portable Discrete Sampler, Operation and Service Manual, Nov. 1977, 52 pp.

* cited by examiner

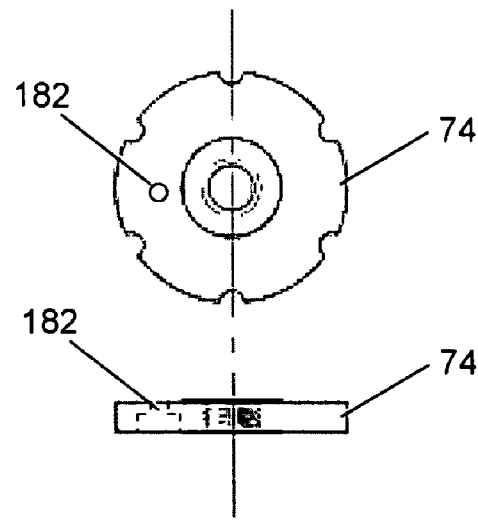
FIG. 9B
FIG. 9C
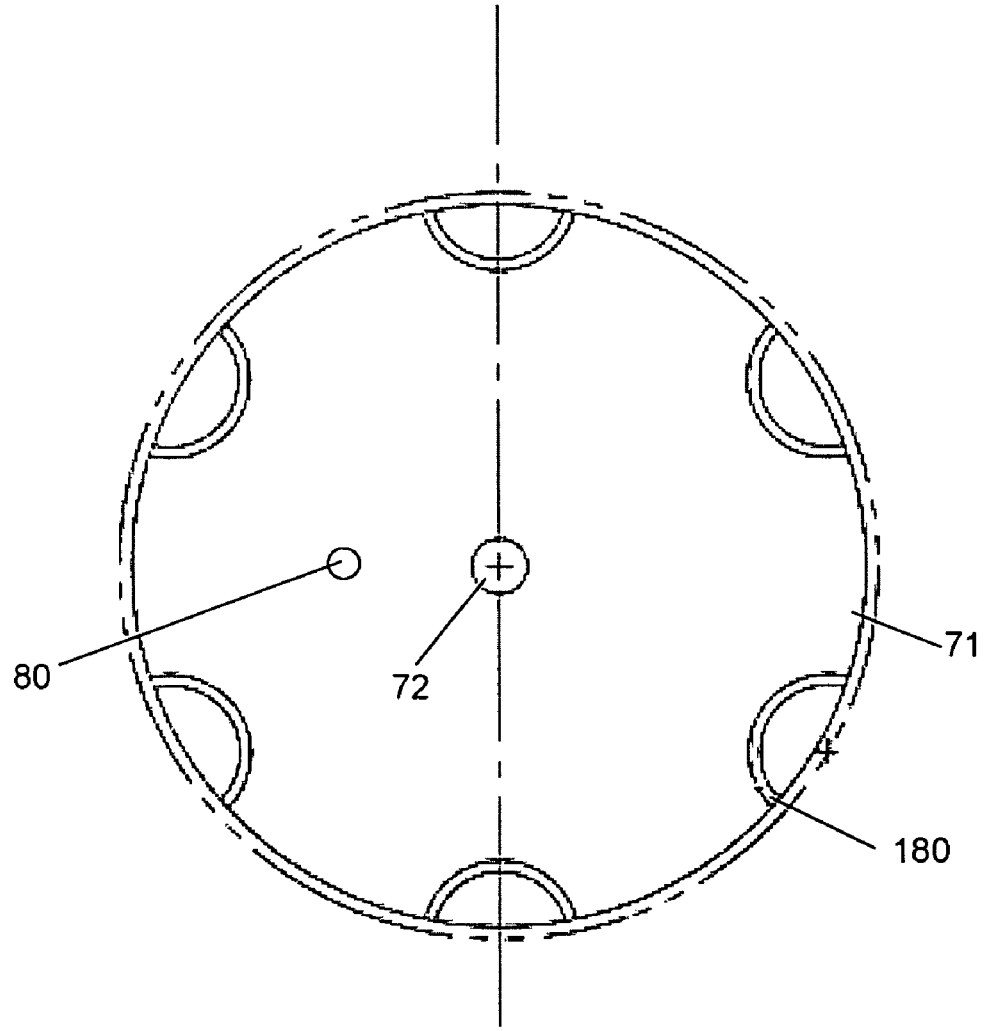
FIG. 9A

US 8,051,727 B1

PORE-WATER PROFILER

STATEMENT OF GOVERNMENT INTEREST

The invention described herein may be manufactured and used by or for the Government of the United States of America for government purposes without the payment of any royalties therefore.

BACKGROUND

1. Field of the Invention

The invention relates in general to a fluid sampler and, more particularly, to an in situ, clog-resistant pore-water sampler for use in collecting water samples to determine depth profiles of chemical constituents across a sediment-water interface.

2. Description of the Related Art

Fluid sampling may be used to monitor environmental changes in water, air, or other desired fluids, and to monitor water quality in ground water and surface water. For example, it is desirable to estimate the potential importance of solute flux from the benthos in aquatic systems where long-term (decadal) sediment accumulation of nutrients or toxic substances are of concern. More information regarding the determination of benthic flux in aquatic systems is found in J. S. Kuwabara et al., "Quantifying the Benthic Source of Nutrients to the Water Column of Upper Klamath Lake, Oreg.," *U.S. Geological Survey Open File Report* 2007-1276, 39 pp., 2007, incorporated herein by reference.

Conventional techniques used to sample pore water to quantify the benthic flux of biologically reactive solutes across the sediment-water interface are labor, equipment, and resources demanding. Also, where sediment is dominated by fines (less than 63-micron particles), particularly detrital fines with high-organic content (e.g., in eutrophic, lentic environments), conventional samplers can quickly clog to yield inadequate sample volumes.

Therefore, there is a need for a simple, inexpensive, reliable, remote sampling device for use in obtaining test samples of a fluid medium for major and trace solutes from remote sites that will not clog when obtaining samples from fine, organic-rich sediments.

BRIEF SUMMARY OF THE INVENTION

Water-quality managers and modelers often require measurements of benthic flux to comprehensively and accurately represent the transport of toxic and nutritive substances in surface waters. The pore-water profiler described below is a cost-effective field device to respond to such requirements for a wide range of environmentally significant solutes that are transported across the sediment-water interface.

The non-metallic pore-water profiler described herein provides pore-water samples near the sediment-water interface to produce high-resolution (centimeter-scale) vertical concentration profiles for trace solutes, even when the bed material is dominated by fine or organic-rich particles that tend to clog filters and screens. The pore-water profiler is suitable for investigations involving a wide variety of biologically reactive solutes (e.g., micronutrients, macronutrients, and toxic trace metals), some requiring ultra-clean sampling protocols. Concentration profiles can then be used to determine a diffusive flux of solute across the sediment-water interface. Particularly in lentic systems, this benthic flux has been demonstrated to be a significant if not dominant source of biologically reactive solute to the water column. In addition, samples collected by the pore-water profiler have been found to be suitable for analysis of other solutes of environmental interest (e.g., dissolved organic carbon).

The pore-water profiler is deployed and triggered to collect filtered pore water from variable depths above and below the sediment-water interface. The profiler collects the filtered pore water through a series of sintered porous polyethylene probes and in-line filters to avoid the problem of sample syringes that become plugged with fine sediments. Unlike conventional samplers, the pore-water profiler is suitable for trace-solute analyses because all wetted surfaces are acid-washable.

BRIEF DESCRIPTION OF THE DRAWINGS

Various aspects and advantages of the invention will become apparent from the following detailed description, taken in conjunction with the accompanying drawings, which are not necessarily drawn to scale.

FIG. 9A is a bottom view of an upper plate;

FIG. 9B is a top view of a retaining nut; and

FIG. 9C is a side view of the retaining nut shown in FIG. 9B.

DETAILED DESCRIPTION OF THE PREFERRED EMBODIMENTS

Figure 1:
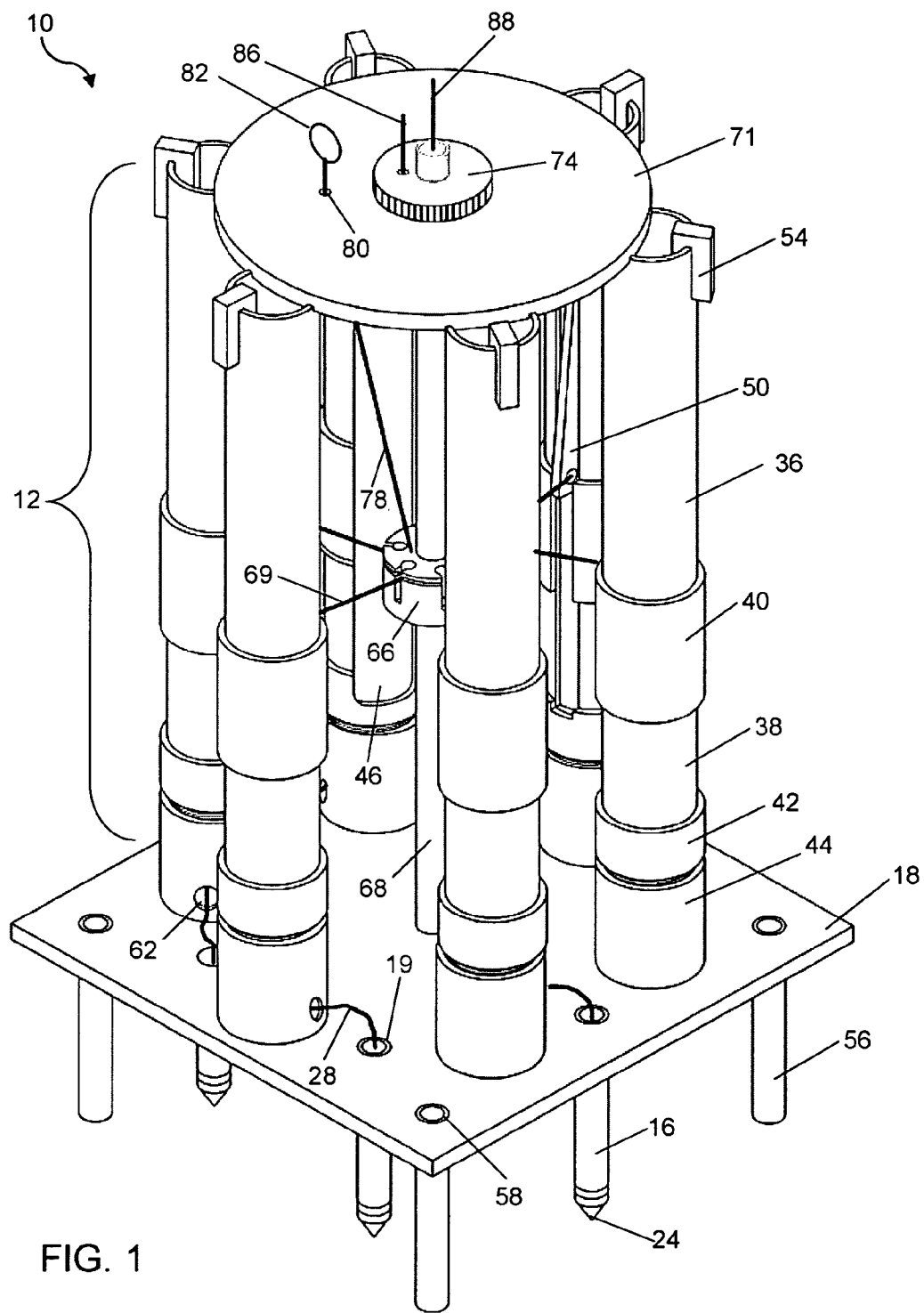
FIG. 1 is a perspective view illustrating a pore-water profiler according to an embodiment of the invention.

An exemplary embodiment of a pore-water profiler 10 is illustrated in FIG. 1. The pore-water profiler 10 (also referred to as a "fluid sampler") is a non-metallic field-sampling device with one or more towers 12, each tower 12 (also referred to as a "sampling circuit housing") housing a portion of a sampling circuit 14 (see FIG. 2). Each sampling circuit 14 is exposed to the water column and collects pore water from a defined depth relative to the sediment-water interface. All sample-wetted parts are acid-washable and hence compatible with studies involving trace-inorganic solutes.

Figure 2:
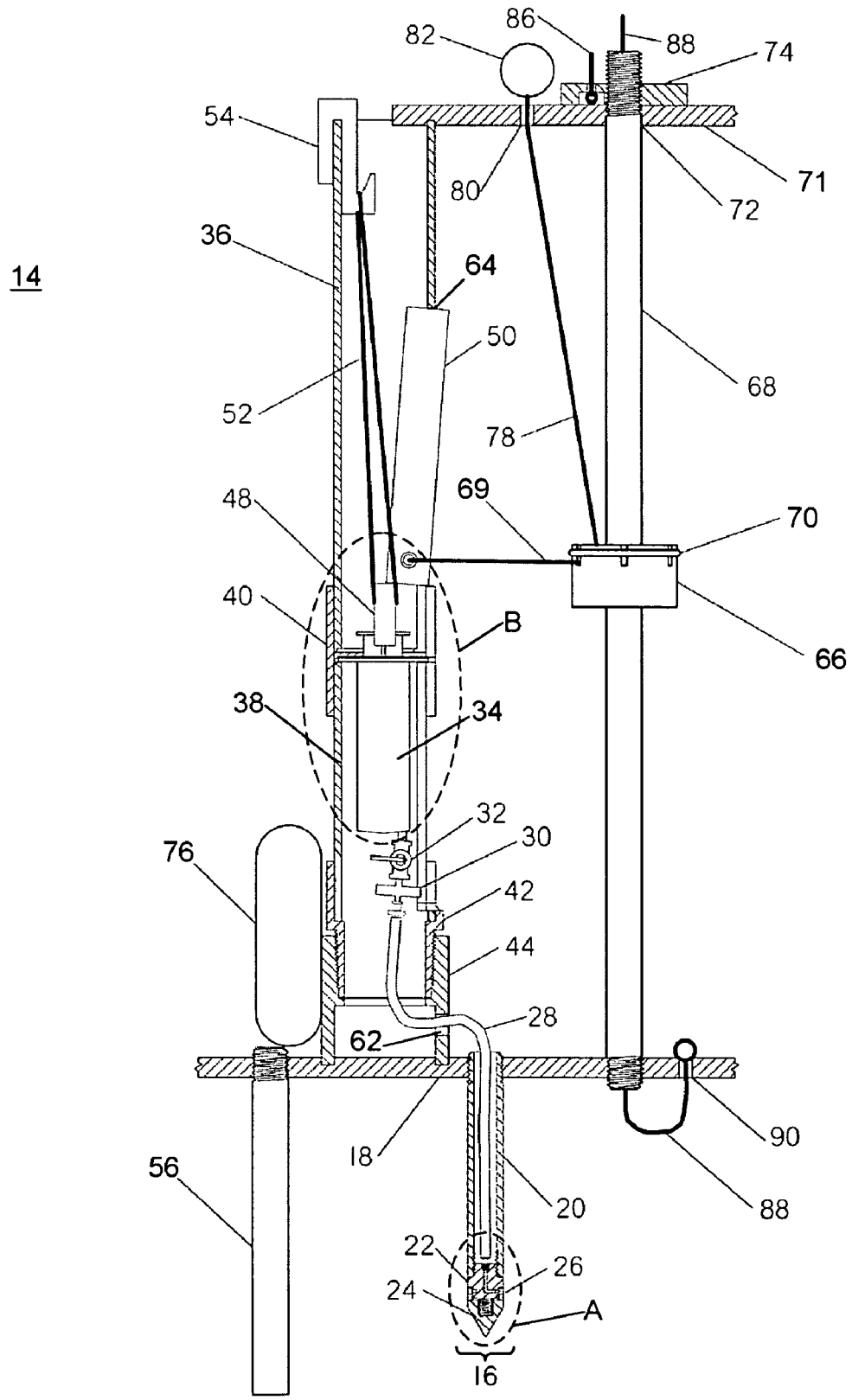
FIG. 2 is an elevational view of a sampling circuit according to the embodiment of the invention.
Figure 3:
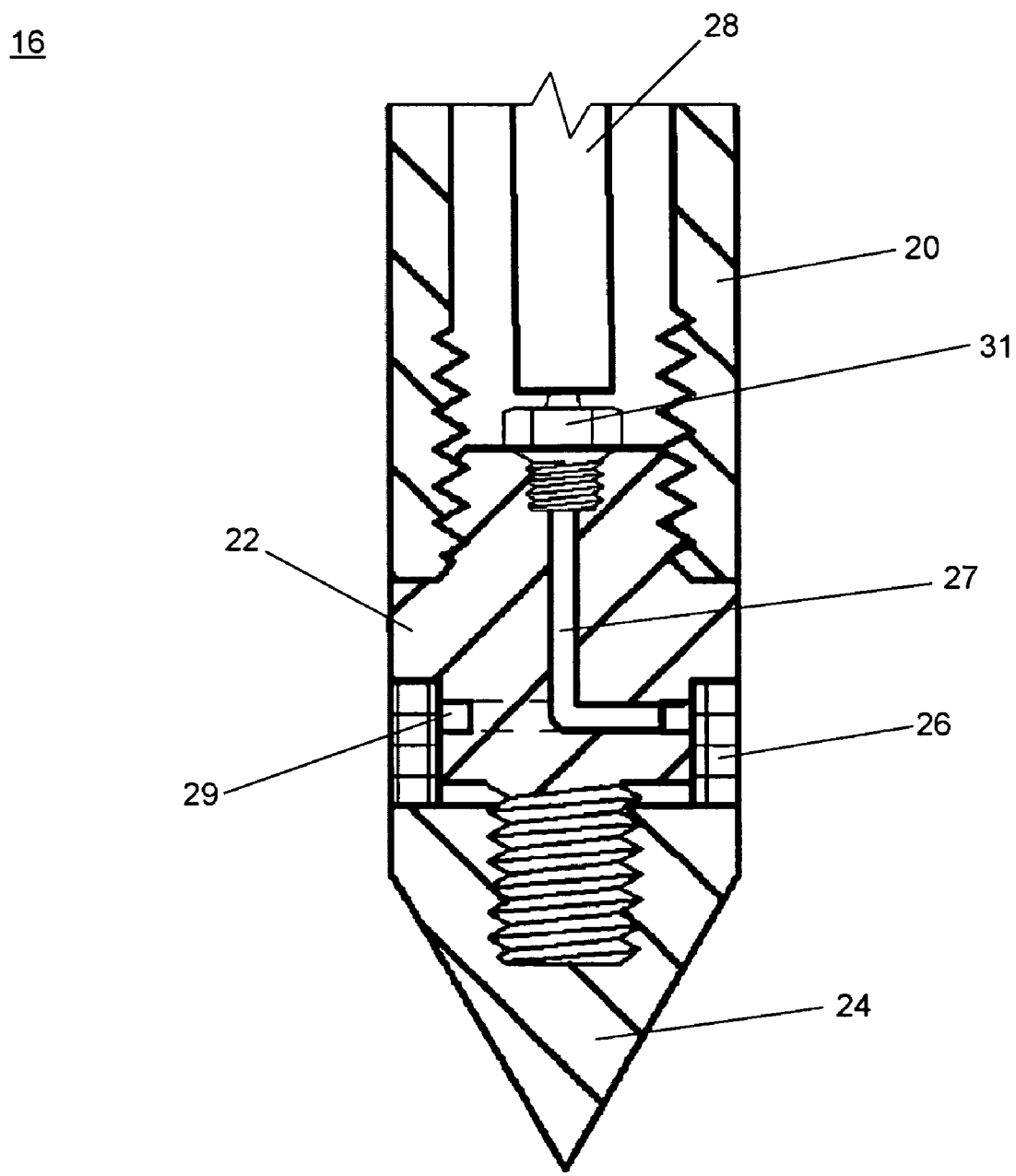
FIG. 3 is an enlarged view of portion A of FIG. 2.
Figure 4:
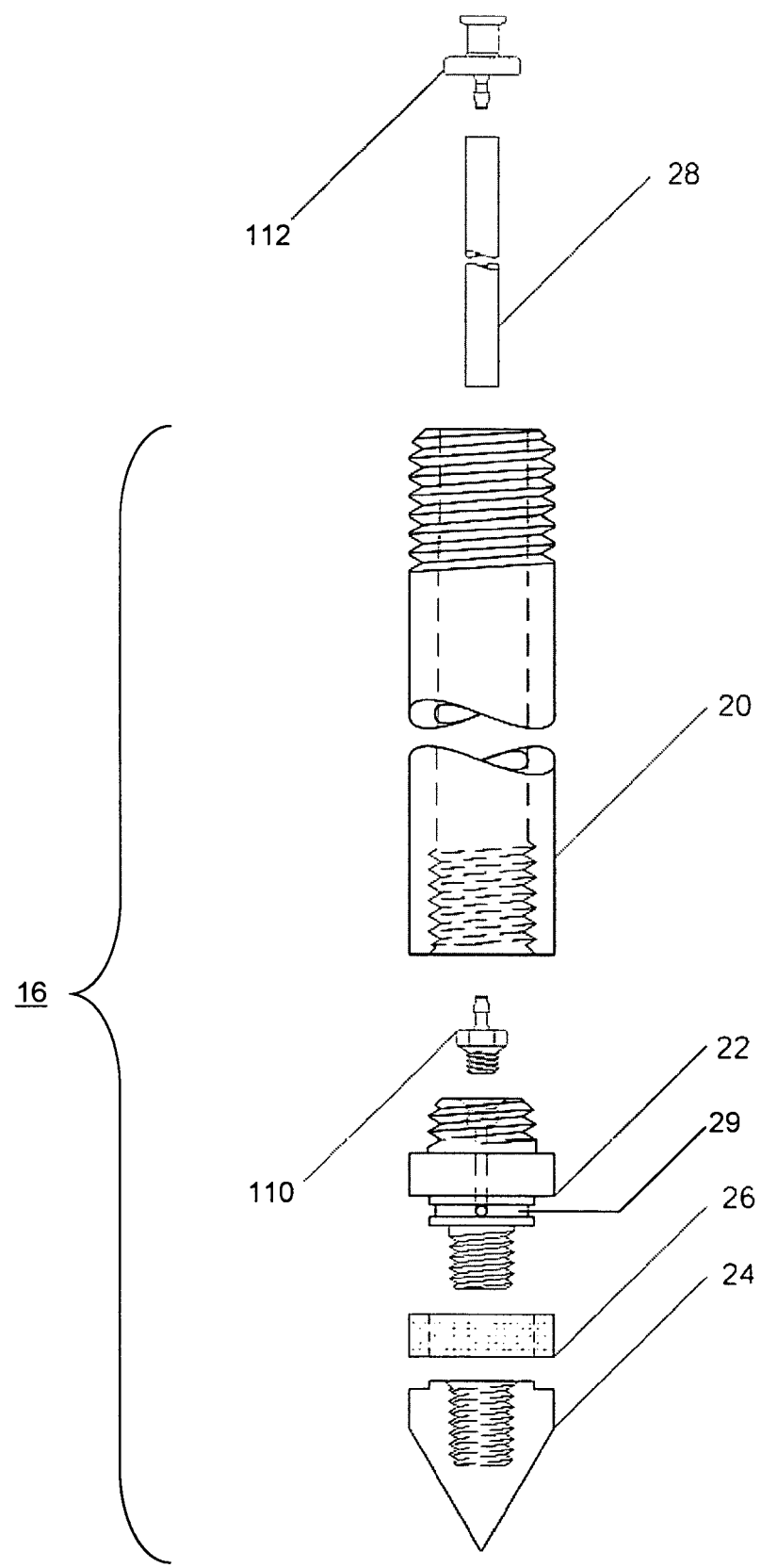
FIG. 4 is an exploded view of portion A of FIG. 2.

In the embodiment shown in FIG. 1, the pore-water profiler 10 includes six independent sampling circuits 14. FIG. 2 illustrates only one of the sampling circuits 14 for clarity. The other sampling circuits are similar. Each sampling circuit 14 includes a probe 16 (also referred to as a "sample intake probe") that is connected to a lower plate 18 through an opening 19. The lower plate 18 is preferably made of polyvinyl chloride (PVC). An enlarged view of the probe 16 is shown in FIG. 3. An exploded view of the probe 16 is shown in FIG. 4. The probe 16 includes a probe stem 20, an inner probe fitting 22, an outer probe fitting (also referred to as a "tip") 24, and a filter 26. The filter 26 is preferably a sintered porous polyethylene ring 26.

The probe stem 20 has external threads to connect to the lower plate 18 and internal threads to receive the inner probe fitting 22. The probe stem 20 is preferably made of polypropylene. The tip 24 is preferably made of polyvinylidene difluoride (PVDF) and is conical to facilitate sediment penetration, but may be flattened or rounded. The sintered porous polyethylene ring 26 is slipped over the threaded upper perimeter of the tip 24, and the tip 24 is attached to the bottom of the inner probe fitting 22. The sintered porous polyethylene ring 26 is preferably made from a porous, 30-micron polyethylene pipe. Pore water enters the probe 16 through the sintered porous polyethylene ring 26, which filters the pore water. The length of each probe stem 20 may be varied to place each sintered porous polyethylene ring 26 at a desired sediment depth.

The inner probe fitting 22 is preferably made from a 25-mm PVDF rod. The inner probe fitting 22 is both threaded and bored to create a channel 27 to transfer pore water from the sintered porous polyethylene ring 26 to an acid-washed tube 28. The inner probe fitting 22 also has a groove 29 cut circumferentially to receive the pore water from the sintered porous polyethylene ring 26. The tube 28 transfers the pore water to an in-line filter 30 (see FIG. 2). The tube 28 is connected to the inner probe fitting 22 and the in-line filter 30 using commercially available barbed fittings 110 and 112, respectively, which are preferably made of PVDF. The tube 28 may be made of, for example, Viton® or C-Flex® tubing.

Referring back to FIG. 2, the in-line filter 30 is preferably a 0.2-micron filter and has a membrane composition that is selected based upon the solutes of interest. For example, hydrophilic PVDF (polyvinylidene fluoride) membranes are acid-washable and may be useful for trace-inorganic solutes. Filtrate from the in-line filter 30 then passes through a commercially available plastic valve 32 into a sample container 34. In the embodiment shown in FIG. 2, the sample container 34 is a commercially available all plastic 60-mL syringe 34. The volume held by each syringe 34 can be selected based on the intended application. For example, a typical commercially available all plastic syringe can hold a volume of up to 60 mL. Alternatively, different-sized syringes may be used with the pore-water profiler 10.

Figure 5:
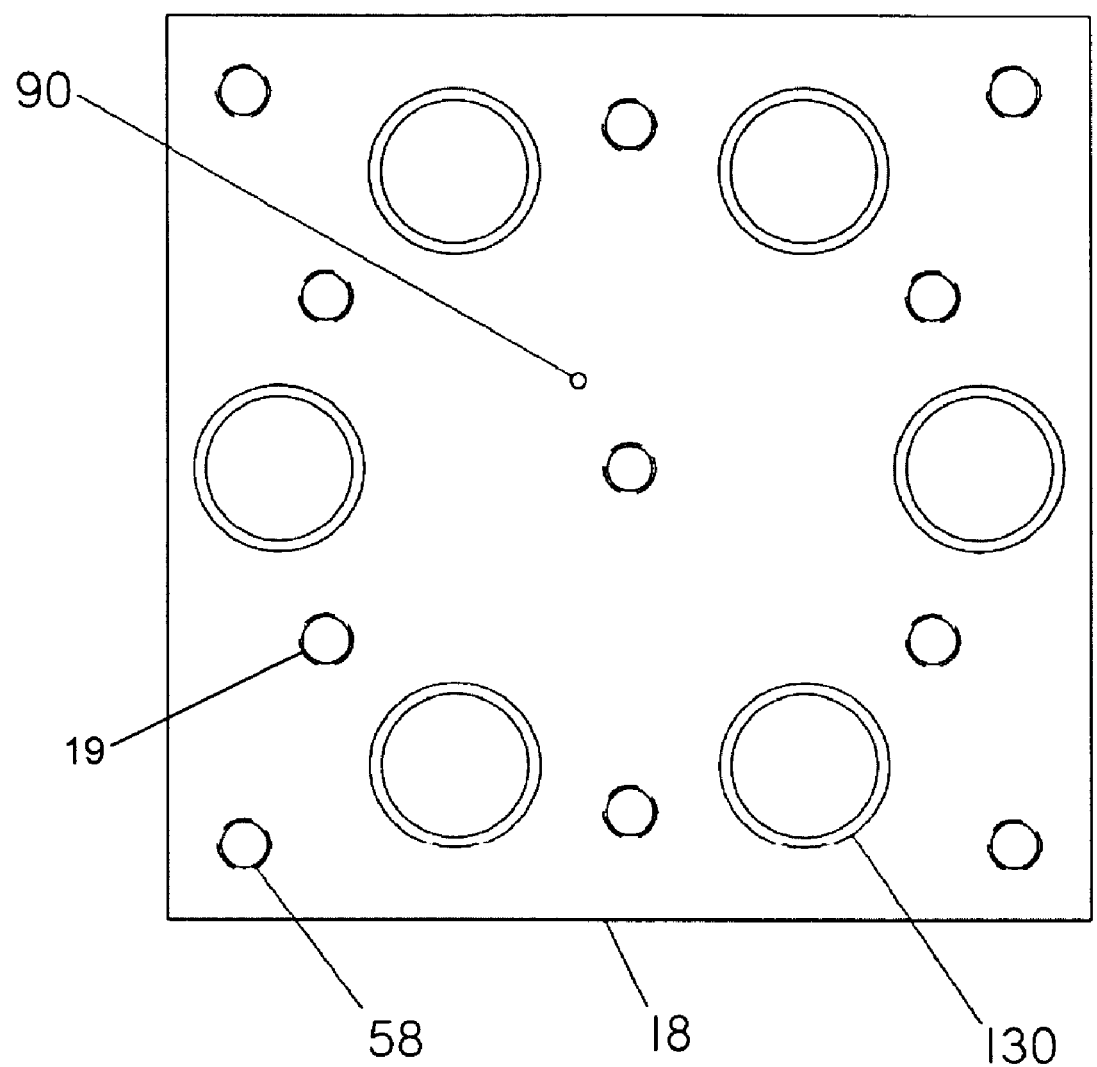
FIG. 5 is a top view of a lower plate.

Referring to FIGS. 1 and 2, each of the sampling circuits 14 is supported above the lower plate 18 by one of the towers 12. In the embodiment shown in FIGS. 1 and 2, each tower 12 includes an upper tower member 36, a lower tower member 38, a tower union 40, a lower tower member stop 42, and a tower base 44. The upper tower member 36, the lower tower member 38, and the tower union 40 are preferably made from a transparent PVC pipe to aid in viewing assembly of the pore-water profiler 10 and subsequent sample retrieval. For example, the upper tower member 36 and the lower tower member 38 may be made from 2-inch PVC pipe, and the tower union 40 may be made from a 2-inch PVC pipe coupling. The tower base 44 and the lower tower member stop 42 are preferably made from PVC. After the upper tower member 36, the lower tower member 38, and the tower union 40 are joined together (e.g., by adhesively affixing the tower union 40 to the upper tower member 36 and the lower tower member 38), a portion is cut out or removed to create a vertical slot 46 that facilitates access to and assembly of the sampling circuits 14 and sample retrieval. The lower tower member 38 rests in the lower tower member stop 42, and the lower tower member stop 42 is attached to the lower plate 18 through the tower base 44, which is attached to the lower plate 18. The tower bases 44 may be attached to the lower plate 18, for example, by being affixed to grooves 130, as shown in the embodiment of the top side of the lower plate 18 in FIG. 5. The grooves 130 form seats for attaching (e.g., by cementing) the tower bases 44 to the lower plate 18.

Figure 6:
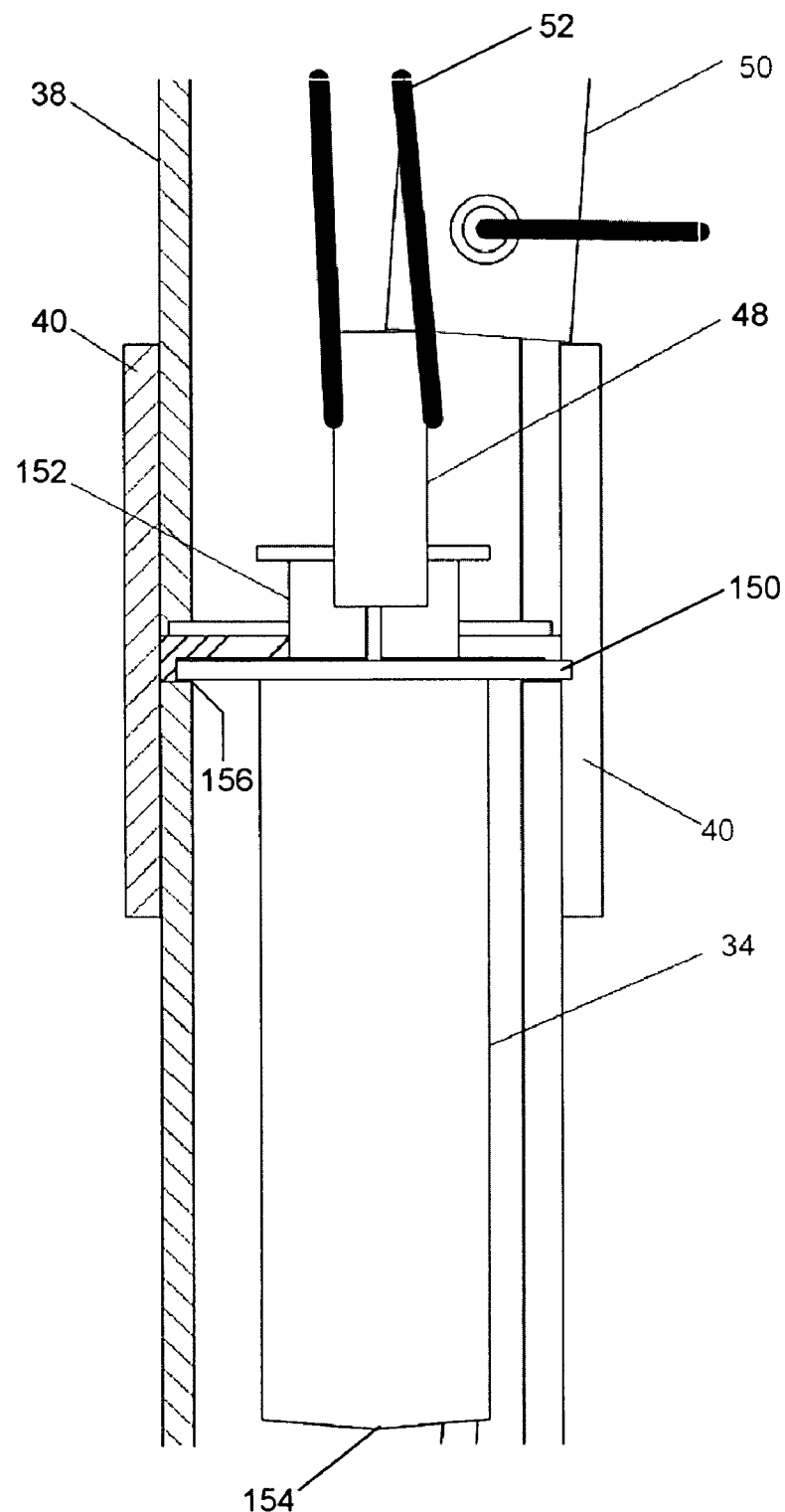
FIG. 6 is an enlarged view of portion B of FIG. 2.
Figure 7A:
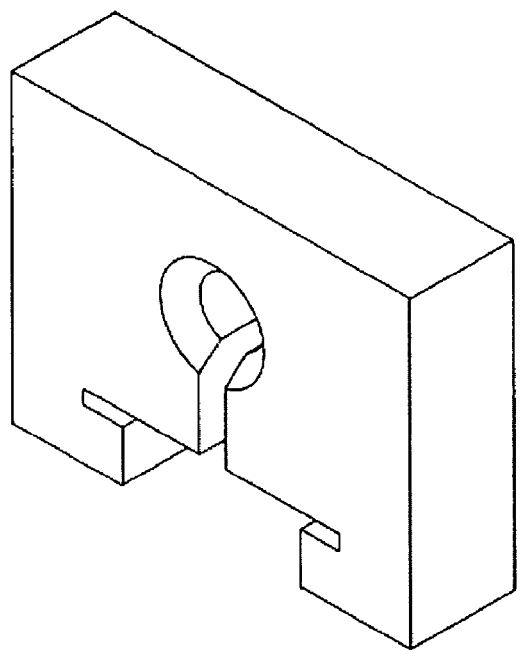
FIG. 7A is a perspective view of a bracket.
Figure 7B:
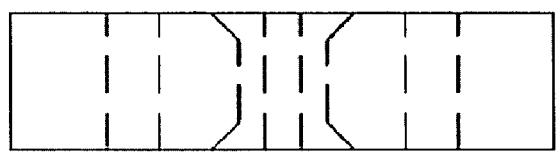
FIG. 7B is a top view of the bracket shown in FIG. 7A.
Figure 7C:
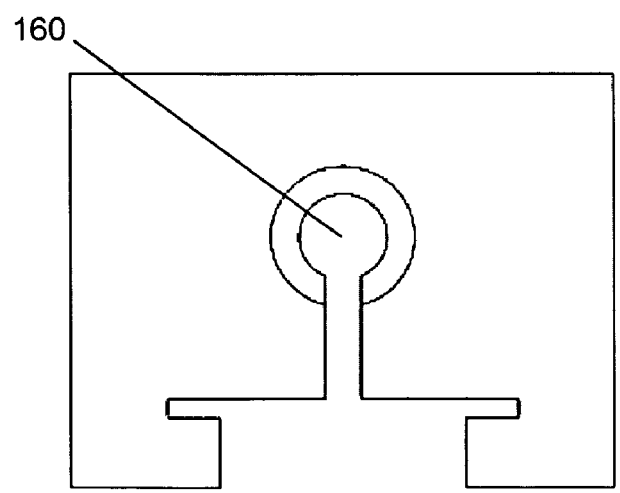
FIG. 7C is a front view of the bracket shown in FIG. 7A.
Figure 7D:
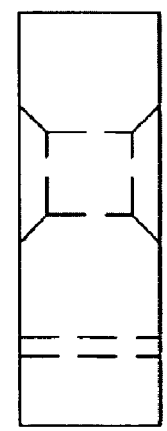
FIG. 7D is a side view of the bracket shown in FIG. 7A.

An enlarged view of the syringe 34 within the tower 12 is shown in FIG. 6. The syringe 34 includes a flange 150, a plunger 152, and a syringe tip 154. Within each tower 12, slots 156 are provided to slide the syringe flange 150 in place with the syringe tip 154 and the valve 32 facing in a downward direction. A bracket 48 is slid onto the top of the syringe plunger 152. The bracket 48 is preferably made of PVC and is illustrated in more detail in FIGS. 7A to 7D. Referring to FIGS. 2 and 7C, a spacer rod 50 presses against the bracket 48 to hold the syringe plunger 152 in position until the pore-water profiler 10 is triggered. The spacer rod 50 is preferably made of PVC. Elastomeric rings 52 are slipped into a central hole 160 of the bracket 48 and are connected to the top of the tower 12 to generate tension on the syringe plunger 152. In the embodiment shown in FIG. 2, the elastomeric rings are rubber o-rings 52, which are connected to the top of the tower 12 using a hook 54 that hangs from the top of the upper tower member 36. The hooks 54 are preferably made of PVC.

Referring back to FIG. 1, the pore-water profiler 10 is assembled from the lower plate 18 upward before being deployed. To aid assembly, the lower plate 18 is supported at four corners by legs 56 that attach to the lower plate 18. The legs 56 may optionally be removed to facilitate sampling. The legs 56 are preferably made of PVC and are threaded to attach to the lower plate 18 through openings 58. The lower tower member stops 42 are attached to the tower bases 44 on the lower plate 18, and the lower tower member 38, which has been affixed to the tower union 40 and the upper tower member 36, is placed in the lower tower member stop 42. Then, the probes 16 are attached to the under side of the lower plate 18 through the openings 19.

Referring to FIG. 2, for each tower 12, one end of the tube 28 is fed through the probe 16, and the other end is fed through an opening 62 in the tower base 44, into the lower tower member 38, to the in-line filter 30. The acid-washed syringe 34, filled with 10 Mohm double-dionized water, is emptied through the sampling circuit 14 for a final rinse of all acid-washed, wetted parts. The syringe 34 is secured in the tower slots 156 as described above and the bracket 48 with the o-rings 52 is slid onto the syringe plunger 152. The lower end of the spacer rod 50 is placed against the bracket 48 and the upper end abuts the top 64 of the vertical cutout 46 to secure the position of the syringe plunger 152 before the pore-water profiler 10 is triggered.

Figure 8A:
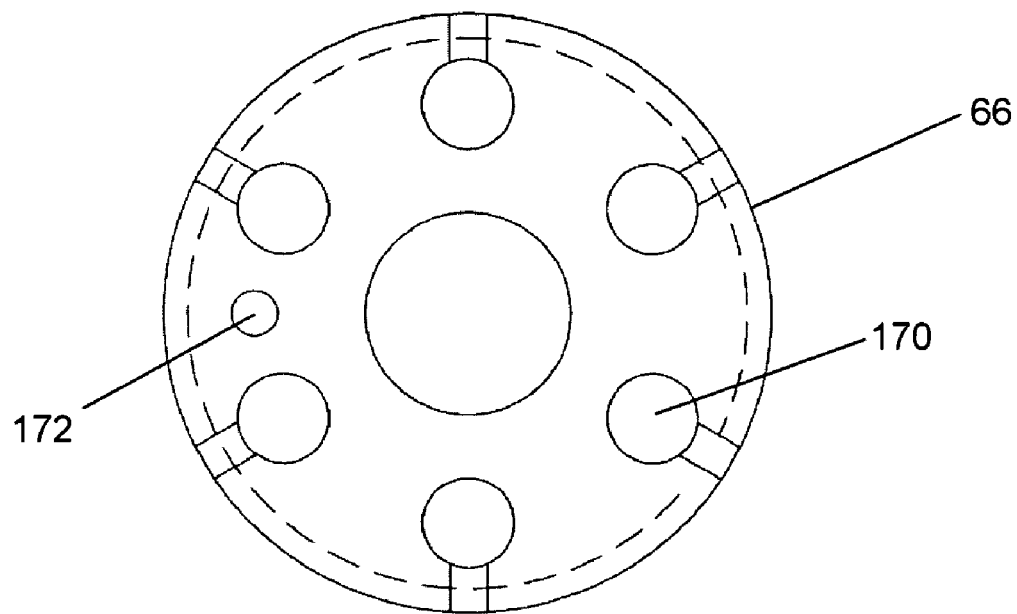
FIG. 8A is a top view of a disk.
Figure 8B:
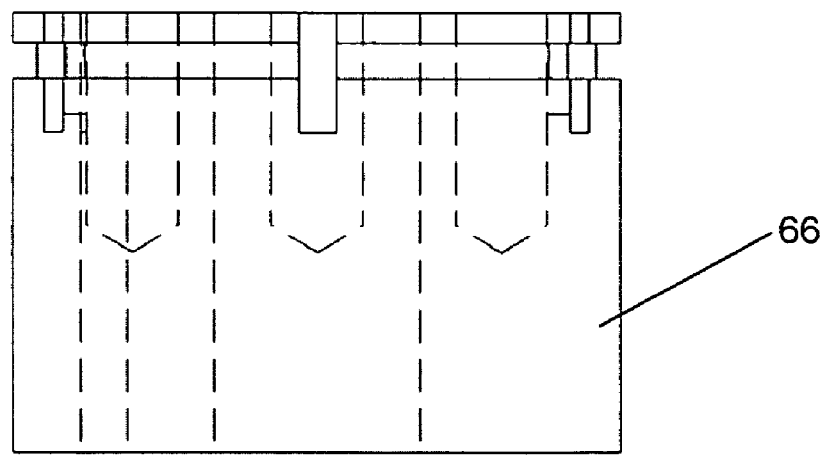
FIG. 8B is a side view of the disk shown in FIG. 8A.

The o-rings 52 are extended from the bracket 48 onto the hooks 54 hanging off the walls of the upper tower members 36. Tension from the o-rings 52 pulls on the syringe plungers 152 to collect the samples after the pore-water profiler 10 is triggered. The end of each spacer rod 50 touching the bracket 48 is connected to a central hub 66 that slides along (i.e., up and down) a central pipe 68 (also referred to as a "central support"). In the embodiment shown in FIGS. 1 and 2, the central hub 66 is a disk 66, and the spacer rod 50 is tied to the disk using a line 69, preferably a ⅛-inch nylon cord. The central disk 66 is illustrated in more detail in FIGS. 8A and 8B. In the embodiment of the central disk 66 shown in FIGS. 8A and 8B, the ends of the lines 69 are knotted to secure each into one of six vertical holes 170. The lines 69 are further secured in the central disk 66 with an o-ring 70 placed around the central disk 66. The central disk 66 is preferably made of PVC. The central pipe 68 is preferably made of PVC and is threaded to attach to the lower plate 18, as shown in FIG. 2.

As shown in FIGS. 1 and 2, an upper plate 71 is placed on the tops of the upper tower members 36 after all of the sampling circuits 14 have been assembled. In the embodiment of the upper plate 71 shown in FIG. 9A, the under side of the upper plate 71 has grooves 180 to receive the upper tower members 36. Referring to FIGS. 1 and 2, the upper end of the central pipe 68 is fed through an opening 72 in the upper plate 71. The upper tower members 36 and the upper plate 71 are secured with a fastener 74. In the embodiment shown in FIGS. 1 and 2, the fastener 74 is a retaining nut 74. The retaining nut 74 is preferably made of PVC and is shown in more detail in FIGS. 9B and 9C. Plastic-coated weights 76 are secured to the pore-water profiler 10 (e.g., by being tied onto the tower bases 44) to control buoyancy.

In addition to the line 69 that connects the spacer rod 50 to the central disk 66, several additional lines are used to deploy the pore-water profiler 10, as shown in FIGS. 1 and 2. A first line 78 is attached to the central disk 66 through a hole 172 (see FIG. 8A), fed through an opening 80 in the upper plate 71, and connected to a top ring 82. A trigger line (not shown) is fed through the top ring 82 so that when quickly tugged, all the spacer rods 50 are dislodged and sample collection in all of the sampling circuits 14 begins. Alternatively, the pore-water profiler 10 may be adapted so that other forms of energy may be used to trigger the pore-water profiler 10. For example, a plastic or plastic-coated spring may be used rather than the o-rings 52. A buoy line 86 connects to the retaining nut 74 on the upper plate 71 through a hole 182 (see FIGS. 9B and 9C) and to a buoy (not shown) to keep the pore-water profiler 10 vertical while deployed. A tether line 88 is fed through the central pipe 68 and secured to the lower plate 18 through an opening 90 in the lower plate 18. The pore-water profiler 10 is lowered onto the bottom sediment using the tether line 88, after which the trigger line is tugged and pulled out of the water. The tether line 88 may be secured to another buoy (not shown) to facilitate retrieval of the pore-water profiler 10.

Upon retrieval of the pore-water profiler 10, each of the valves 32 is shut, and the sample syringes 34 are removed from the towers 12 and doubled bagged in argon-filled, plastic, zipped bags. Argon-filled bags containing the filtered samples are then transported to the laboratory in refrigerated coolers for chemical analyses.

In one embodiment of the invention, in addition to sampling the water just above (approximately 1 centimeter) the sediment-water interface, the pore-water profiler 10 was used to collect interstitial water from five depths within the top 10 centimeters of a lakebed, with the length of the probe stems 20 being varied to place the sintered porous polyethylene rings 26 at 1.0, 2.0, 3.3, 5.5, and 10.0 cm, to characterize dissolved solute vertical gradients (that is, six independent sampling circuits 14). Each sampling circuit 14 collected filtered (0.2 micron) water into acid-washed 60 mL syringes 34. After being lowered onto the lakebed, the pore-water profiler 10 was tripped mechanically to begin sample collection and retrieved approximately 24 hours later. Dye experiments indicated that this extended sampling period avoided short circuiting of samples between depths and along pore-water profiler 10 surfaces. After retrieval, the valves 32 for the sample syringes 34 were closed, placed in argon-filled bags, and refrigerated in darkness for subsequent chemical analyses.

The pore-water profiler described herein provides numerous benefits. For example, in a single deployment, the profiler collects multiple pore-water samples from different depths to generate a high-resolution (centimeter-scale) vertical concentration profile, minimizing relative errors between depths. This permits the determination of diffusive-flux measurements for solutes.

The sequential filtration of pore water avoids the problem of sample-circuit clogging, even in sediments dominated by fine or organic-rich particles that would typically plug sample-collection ports of conventional samplers.

The pore-water profiler is non-metallic with wetted parts (i.e., parts exposed to the sample) that are all acid-washable. No electronic or motorized parts are used to avoid sample contamination by exposed metal parts. As all parts exposed to the sample are acid-washable, the pore-water profiler is suitable for trace-inorganic studies requiring ultra-clean (sub-micromolar) sampling techniques. In addition, samples collected by the pore-water profiler have been found to be suitable for analysis of other solutes of environmental interest (e.g., dissolved macronutrients and organic carbon).

The pore-water profiler collects the pore-water sample directly (in situ) without the need for an ultra-clean field laboratory to process the samples. The filtered sample retrieved from each sampling circuit can be transported directly from the field for chemical analysis, which minimizes the potential for field contamination of samples and minimizes sample-storage time where particulate matter may alter the speciation or partitioning (i.e., the chemical forms) of the analytes. The direct sampling afforded by the pore-water profiler permits greater spatial and temporal coverage (i.e., less field time and effort is required to collect the sample). No incubation experiments are needed. Facilities are often not available, or too resource-intensive to construct, to perform core extrusion studies. The pore-water profiler offers a convenient and cost-effective alternative.

Benthic-flux measurements have been determined by various methods, but are consistently resource intensive. Because all of the parts can be machined from commercially available stock or purchased directly, the pore-water profiler can cost-efficiently provide spatial and temporal coverage of a wide range of aquatic systems where contaminants may accumulate and remobilize in, and transport from, benthic sediments.

The pore-water profiler described herein, is easily assembled, disassembled, transported, and deployed. Because the pore-water profiler does not require the use of any heavy equipment (e.g., a high-speed centrifuge, pump, motor, etc.), the pore-water profiler is a stand alone device that can be carried by one person for field deployment to determine pore-water concentration gradients.

Although the invention has been described relative to a specific embodiment thereof, it is not so limited and many modifications and variations thereof will be readily apparent to those skilled in the art in light of the above teachings. For example, the lengths of the probe stems 20 can be modified (lengthened) so that the profiler can sample the water column of a lake or estuary. Such water-column profiles have been used to estimate benthic flux by eddy diffusivity. Similar stem-length modifications can be employed to sample the air column, using a suspended profiler.

These and other variations and modifications of the illustrated embodiment will become readily apparent to those skilled in the art in light of the above teachings without departing from the spirit and scope of the present invention. It is therefore to be understood that within the scope of the appended claims the invention may be practiced otherwise than as specifically described.

What is claimed is:

1. A pore-water sampler for collecting pore-water samples at desired depths above and below a sediment-water interface, the pore-water sampler comprising:
    a plurality of sample intake probes, each sample intake probe receiving a separate pore-water sample and each sample intake probe comprising:
        an inner probe fitting having an opening on an outer wall thereof to receive the pore-water sample, a tip attached to a bottom of the inner probe fitting, the tip being placed in or on bottom sediment of an aquatic system, and a first filter positioned at the bottom of the inner probe fitting above the tip and adjacent to the opening in the outer wall of the inner probe fitting, the first filter providing a first filtering of the respective pore-water sample;

a plurality of second filters respectively connected in-line to the tops of the sample intake probes, the second filters each having a pore size less than a pore size of the first filters and providing a second filtering of the respective pore-water samples;

a plurality of sample containers respectively connected in-line to the second filters to receive, without atmospheric exposure, the pore-water samples filtered by the respective second filters; and a sample triggering system connected to the sample containers to initiate sampling.

2. The pore-water sampler of claim 1, further comprising a lower plate and each sample intake probe further comprising: a probe stem, wherein a top of the probe stem connects to an under side of the lower plates; and a top of the inner probe fitting connects to a bottom of the probe stem, and a top of the tip connects to a bottom of the inner probe fitting with the first filter being positioned between the inner probe fitting and the tip.

3. The pore-water sampler of claim 2, wherein the first filter and the second filter of each sample intake probe form a serial filtration system, and wherein each second filter has a pore size less than a pore size of each corresponding first filter.

4. The pore-water sampler of claim 3, wherein the first filters are sintered porous polyethylene rings that are slipped over an upper perimeter of the respective tips and have pore sizes of approximately 30 microns, and the second filters have membranes with pore sizes of approximately 0.2 microns, the membranes being made from materials selected based upon solutes of interest.

5. The pore-water sampler of claim 4, wherein the probe stems connected to the lower plate have different lengths to position each corresponding sintered porous polyethylene ring at a different desired sediment depth relative to the sediment-water interface, providing high-resolution (centimeter-scale) vertical pore-water profiles.

6. The pore-water sampler of claim 4, further comprising a plurality of tubes, each tube having a first end and a second end, the first ends extending through the probe stems to the inner probe fittings and the second ends connecting to the second filters, respectively, wherein the fluid to be sampled enters the sample intake probes through the sintered porous polyethylene rings, and the inner probe fittings are channeled to transfer the fluid from the sintered porous polyethylene rings to the tubes.

7. The pore-water sampler of claim 6, further comprising an upper plate and a plurality of sampling circuit housings attached to an upper side of the lower plate and to an under side of the upper plate to house the sample containers, the second filters, and an upper end of the tubes, respectively.

8. The pore-water sampler of claim 7, wherein the sample containers are syringes each having a syringe plunger and a flange, and the sampling circuit housings having first slots and second slots above the first slots, the first slots holding the respective syringe flanges.

9. The pore-water sampler of claim 8, wherein the sample triggering system comprises:

a plurality of brackets connected to the respective syringe plungers;

a plurality of elastomeric rings attached respectively to the brackets and to a top of each sampling circuit housing to generate tension on the syringe plungers;

a central support connected to a center of the upper side of the lower plate and the lower side of the upper plate;

a central disk inserted onto the central support that slides up and down the central support;

a plurality of spacer rods each having a first end and a second end, the first ends pressing against the respective brackets and connecting to the central disk, and the second ends being inserted in the respective second slots of the sampling circuit housings; and a top ring inserted through an opening in the upper plate and connected to the central disk, wherein the tension from the elastomeric rings pulls on the syringe plungers, drawing the fluid to be sampled into the sample intake probes when the spacer rods are dislodged by upwardly pulling the top ring.

10. A method of sampling pore-water from a sediment-water interface using a non-metallic pore-water sampler, the method comprising:

assembling a plurality of sample intake probes for the pore-water sampler, each sample intake probe receiving a separate pore-water sample, and assembly of each sample intake probe comprising:

attaching a tip to a bottom of an inner probe fitting having an opening through an outer wall thereof, and positioning a first filter at the bottom of the inner probe fitting above the tip and adjacent to the opening in the outer wall of the inner probe fitting;

connecting a plurality of second filters respectively in-line to the tops of the sample intake probes;

connecting a plurality of sample containers respectively in-line to the second filters;

connecting a sample triggering system to the sample containers;

slowly lowering the pore-water sampler onto bottom sediment of an aquatic system, the tips of the sample intake probes resting in the bottom sediment;

using the sample triggering system to initiate sampling;

filtering, through the first filters, the pore-water that enters the openings in stems of the sample intake probes; and filtering, through the second filters, the pore-water filtered through the first filters and storing the filtered pore-water in the sample containers.

11. The method of claim 10, wherein said filtering, through the first filters, comprises providing each first filter with a pore size of approximately 30 microns, and said filtering, through the second filters comprises providing each second filter with a pore size less than a pore size of the first filters and providing each second filter with a membrane having a pore size of approximately 0.2 microns, the membrane being made from a material selected based upon solutes of interest.

12. The method of claim 10, wherein assembly of each sample intake probe further comprises:

connecting one end of a tube to the inner probe fitting;

connecting the inner probe fitting to a probe stem while sliding the tube through the probe stem; and connecting the other end of the tube to the second filter, the inner probe fitting being channeled to transfer the fluid from the first filter to the tube and a length of the probe stem being selected to position the first filter at a desired sediment depth.

13. The method of claim 10, wherein the sample container is a syringe having a plunger and a flange, and said using the sample triggering system comprises:

connecting a sampling circuit housing to a lower plate of the fluid sampler;
placing the syringe flange in a first slot of the sampling circuit housing;
attaching an elastomeric ring to a bracket;
attaching the bracket to the syringe plunger;
extending the elastomeric ring to a top of the sampling circuit housing;
connecting a central support to a center of the lower plate;
inserting a central disk onto the central support that slides up and down the central support;
pressing a first end of a spacer rod against the bracket and connecting the first end to the central disk, and inserting the second end of the spacer rod in a second slot of the sampling circuit housing above the first slot;
placing an upper plate over the central support and onto the top of the sampling circuit housing;
inserting a top ring through an opening in the upper plate and connecting the top ring to the central disk; and
initiating sampling of the fluid by pulling the top ring to dislodge the spacer rod,
wherein the tension from the elastomeric ring pulls on the syringe plunger, drawing the fluid to be sampled into the sample intake probe when the spacer rod is dislodged from the second slot by upwardly pulling the top ring.

* * * * *